(12) United States Patent
Romero (10) Patent No.: US 8,818,483 B2
(45) Date of Patent: Aug. 26, 2014

(54) METHODS OF MAKING A PADDLE LEAD WITH A CARRIER AND LEADS AND SYSTEMS FORMED THEREBY

(71) Applicant: Boston Scientific Neuromodulation Corporation, Valencia, CA (US)

(72) Inventor: Daniel James Romero, Newhall, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/103,199

(22) Filed: Dec. 11, 2013

(65) Prior Publication Data

US 2014/0180370 A1    Jun. 26, 2014

Related U.S. Application Data

(60) Provisional application No. 61/740,307, filed on Dec. 20, 2012.

(51) Int. Cl.
*A61N 1/05* (2006.01)
*H01R 12/59* (2011.01)
*H01R 43/16* (2006.01)

(52) U.S. Cl.
CPC . *A61N 1/05* (2013.01); *H01R 43/16* (2013.01)
USPC ........... 600/393; 600/395; 600/377; 600/373; 600/372

(58) Field of Classification Search
USPC .......... 607/116; 600/372, 373, 377, 393, 395; 439/55, 884
See application file for complete search history.

(56) References Cited

U.S. PATENT DOCUMENTS

| | | | |
|---|---|---|---|
| 6,181,969 B1 | 1/2001 | Gord | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 7,244,150 B1 * | 7/2007 | Brase et al. | 439/668 |
| 7,437,193 B2 | 10/2008 | Parramon et al. | |
| 7,515,968 B2 | 4/2009 | Metzler et al. | |
| 7,603,178 B2 | 10/2009 | North et al. | |
| 7,672,734 B2 | 3/2010 | Anderson et al. | |
| 7,742,824 B2 | 6/2010 | Skubitz et al. | |
| 7,761,165 B1 | 7/2010 | He et al. | |
| 7,949,395 B2 | 5/2011 | Kuzma | |
| 7,974,706 B2 | 7/2011 | Moffitt et al. | |
| 8,175,710 B2 | 5/2012 | He | |
| 8,224,450 B2 | 7/2012 | Brase | |
| 8,364,278 B2 | 1/2013 | Pianca et al. | |
| 2005/0154435 A1 * | 7/2005 | Stern et al. | 607/116 |
| 2007/0060991 A1 * | 3/2007 | North et al. | 607/117 |
| 2007/0150036 A1 * | 6/2007 | Anderson | 607/116 |
| 2009/0187221 A1 * | 7/2009 | DiGiore et al. | 607/2 |
| 2009/0319013 A1 | 12/2009 | Boling et al. | |

* cited by examiner

*Primary Examiner* — Christopher D Koharski
*Assistant Examiner* — Michael Carey
(74) *Attorney, Agent, or Firm* — Lowe Graham Jones PLLC; Bruce E. Black (57) ABSTRACT

A method of making an electrical stimulation lead includes coupling electrodes to a carrier. The carrier defines at least one set of perforations. The method further includes coupling the electrodes to conductors; forming a flexible paddle sheath over the carrier leaving a stimulation surface of each of the plurality of electrodes exposed; and, after forming the flexible paddle sheath, breaking the carrier along at least one of the at least one set of perforations.

20 Claims, 7 Drawing Sheets

Fig. 5

METHODS OF MAKING A PADDLE LEAD WITH A CARRIER AND LEADS AND SYSTEMS FORMED THEREBY

CROSS-REFERENCE TO RELATED APPLICATIONS

This application claims the benefit under 35 U.S.C. §119 (e) of U.S. Provisional Patent Application Ser. No. 61/740,307 filed Dec. 20, 2012, which is incorporated herein by reference.

FIELD

The present invention is directed to the area of implantable electrical stimulation systems and methods of making and using the systems. The present invention is also directed implantable electrical stimulation leads having a paddle formed using an electrode carrier, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue. Reliability in the manufacture of the leads and, in particular, the reliable and consistent arrangement of electrodes on the lead can be important.

BRIEF SUMMARY

One embodiment is a method of making an electrical stimulation lead including coupling electrodes to a carrier. The carrier defines at least one set of perforations. The method further includes coupling the electrodes to conductors; forming a flexible paddle sheath over the carrier leaving a stimulation surface of each of the plurality of electrodes exposed; and, after forming the flexible paddle sheath, breaking the carrier along at least one of the at least one set of perforations.

Another embodiment is an electrical stimulation lead that includes a paddle body having a carrier and a flexible paddle sheath formed around the carrier. The carrier is broken into at least two pieces. The electrical stimulation lead also includes at least one lead body having a distal end portion, a proximal end portion, and a longitudinal length, the distal ends of each of the at least one lead body coupled to the paddle body; electrodes disposed on the paddle body and coupled to the carrier with each electrode having a stimulation surface that is exposed through the flexible paddle sheath; terminals disposed along the proximal end portions of each of the at least one lead body; and conductors electrically coupling the terminals to the electrodes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed implantable electrical stimulation leads having a paddle formed using an electrode carrier, as well as methods of making and using the leads and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated herein by reference.

Figure 1:
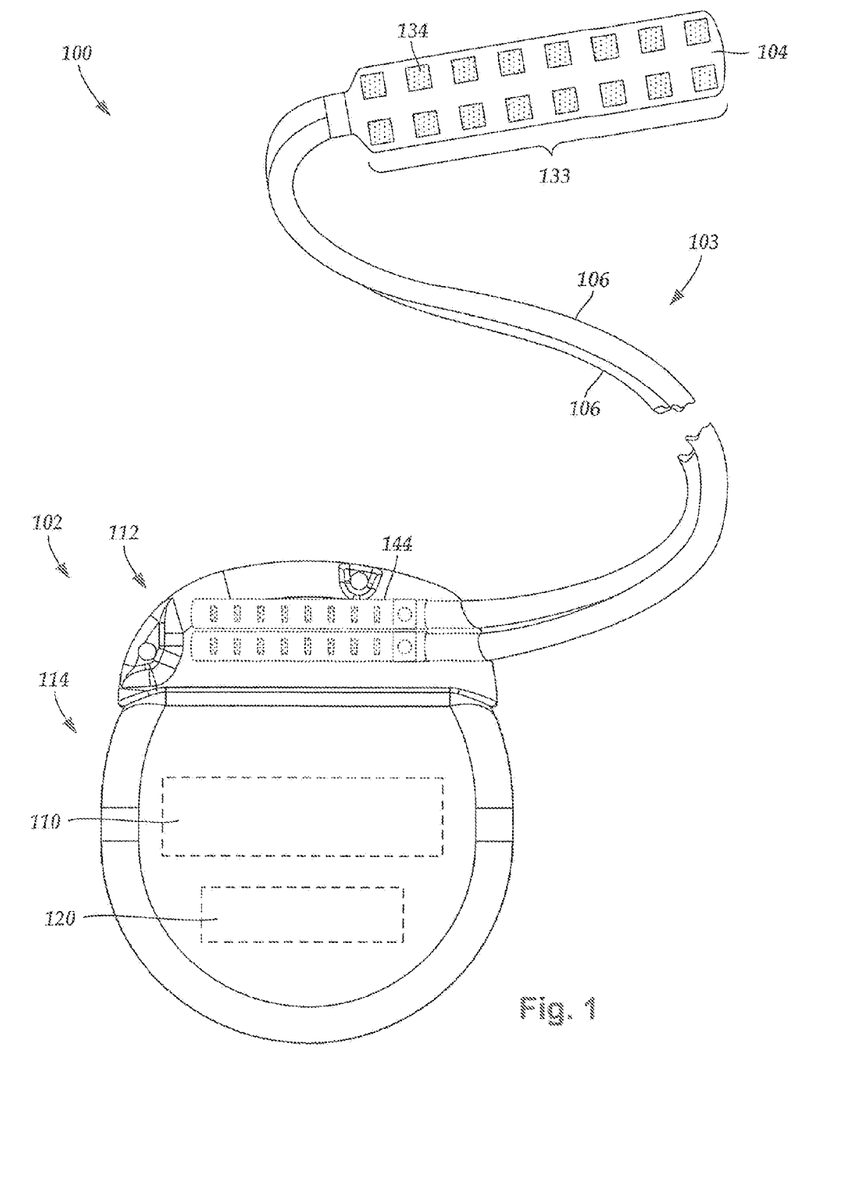
FIG. 1 is a schematic side view of one embodiment of an electrical stimulation system that includes a lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 210 in FIG. 2A-2B) is disposed along each of the one or more lead bodies 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices. For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the paddle body including, for example, four, five, six, seven, eight, nine, ten, eleven, twelve, fourteen, sixteen, twenty-four, thirty-two, or more electrodes 134. The electrodes 134 can be disposed on the paddle body 104 in any suitable arrangement. In FIG. 1, the electrodes 134 are arranged into two columns, where each column has eight electrodes 134.

The electrodes of the paddle body 104 are typically disposed in, or separated by, a non-conductive, biocompatible material such as, for example, silicone, polyurethane, polyetheretherketone ("PEEK"), epoxy, and the like or combinations thereof. The paddle body 104 and the one or more lead bodies 106 may be formed in the desired shape by any process including, for example, molding (including injection molding), casting, and the like. The non-conductive material typically extends from the paddle body 104 to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Figure 2A:
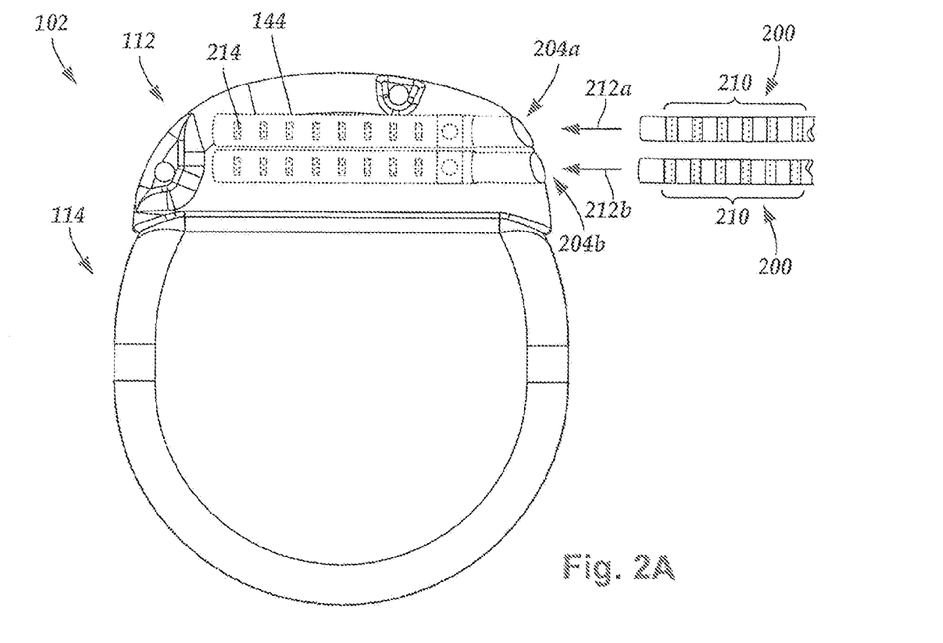
FIG. 2A is a schematic side view of one embodiment of the control module of FIG. 1 configured and arranged to electrically couple to an elongated device, according to the invention.
Figure 2B:
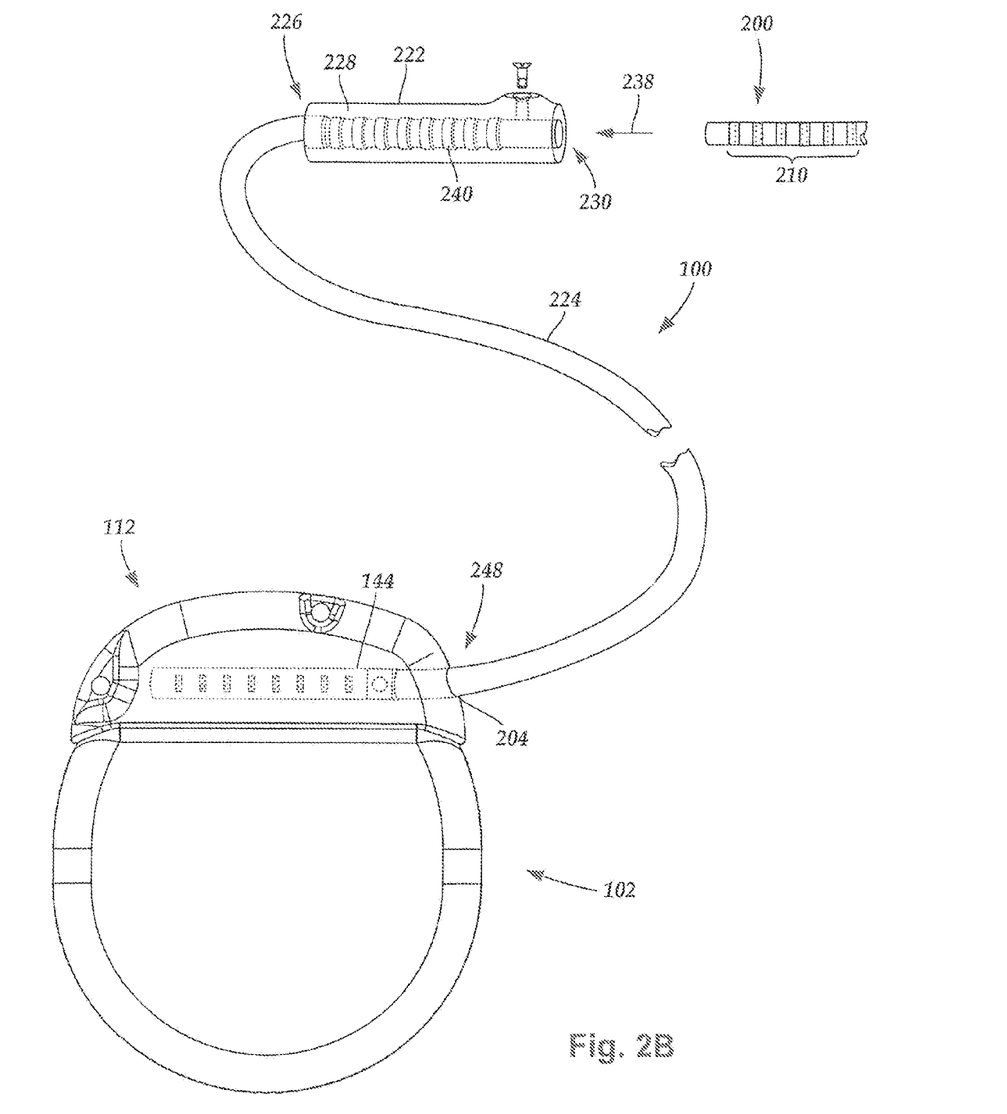
FIG. 2B is a schematic side view of one embodiment of a lead extension configured and arranged to electrically couple the elongated device of FIG. 2A to the control module of FIG. 1, according to the invention.

Terminals (e.g., 210 in FIGS. 2A-2B) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIGS. 2A-2B). The connector contacts are disposed in connectors (e.g., 144 in FIGS. 1-2B; and 222 FIG. 2B) which, in turn, are disposed on, for example, the control module 102 (or a lead extension, a splitter, an adaptor, or the like). Conductors, such as electrically conductive wires, cables, or the like (not shown), extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, one or more of the lead bodies 106 of FIG. 1, one or more intermediate devices (e.g., a splitter, the lead extension 224 of FIG. 2B, an adaptor, or the like or combinations thereof), or a combination thereof.

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., one of the lead bodies 106 of FIG. 1, a splitter, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144 (e.g., the ports 204a and 204b of FIG. 1), or to receive multiple elongated devices 200 (e.g., both of the lead bodies 106 of FIG. 1), or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

One difficulty when manufacturing paddle leads is electrode migration during paddle formation. For example, many paddles are formed by injection molding the paddle material around the electrodes. The injection molding process may result in electrode slippage or migration.

The present invention is directed to using a carrier to which the electrodes are attached or otherwise coupled during paddle formation. The carrier is then broken after the paddle is formed in order to provide flexibility to the paddle.

Figure 3A:
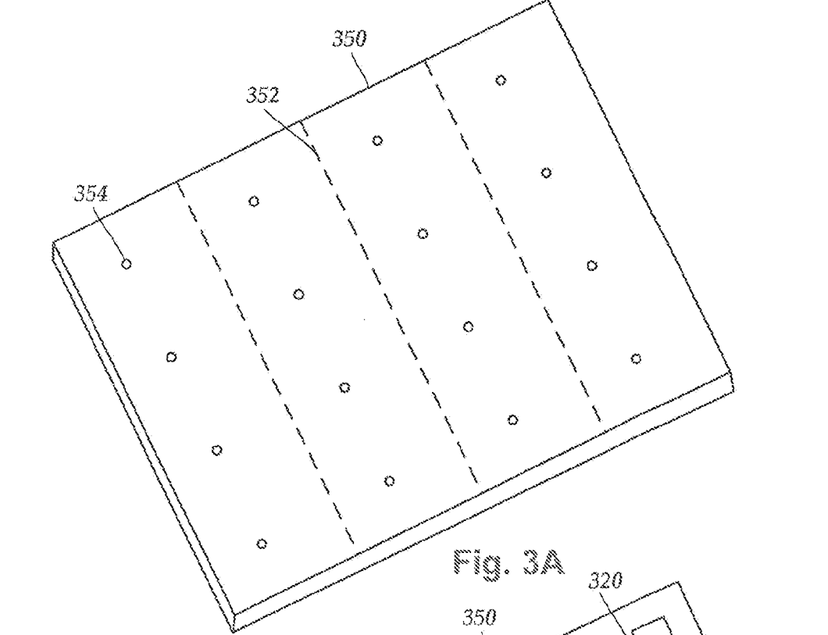
FIG. 3A is a schematic perspective view of one embodiment of a carrier for use in making a paddle of a paddle lead, according to the invention.

FIGS. 3A-3D illustrate steps in one embodiment of a method for the formation of a paddle of a paddle lead. A carrier 350 has perforations 352 and optionally includes holes 354 through the carrier, as illustrated in FIG. 3A. The carrier 350 is made of a non-conductive material that is more rigid than the material forming a flexible paddle sheath around the carrier, as described below. The carrier can be made of, for example, plastic, ceramic, or a non-conductive composite material, or any combination thereof. In at least some embodiments, the carrier is made of a non-conductive composite material that includes metal (e.g., metal particles or metal traces on a substrate) and one or more of plastic or ceramic. In at least some embodiments, the carrier is made of a material that, when broken along the perforations, does not form sharp edges that may damage or penetrate the paddle body that is formed around the carrier.

The perforations 352 in the carrier 350 can take any suitable form. For example, the perforations 352 can take the form of multiple holes passing completely through the carrier 350 along one or more lines. In other embodiments, the perforations 352 can be one or more extended slots passing through the carrier along the one or more lines. In yet other embodiments, the perforations 352 may take the form of one or more indentations that extend into the carrier 350, but not through the carrier, from one or two sides of the carrier along the one or more lines. Any other suitable arrangement that provides a weakened region that can be broken after forming the paddle body can be used as the perforations 352.

Figure 4:
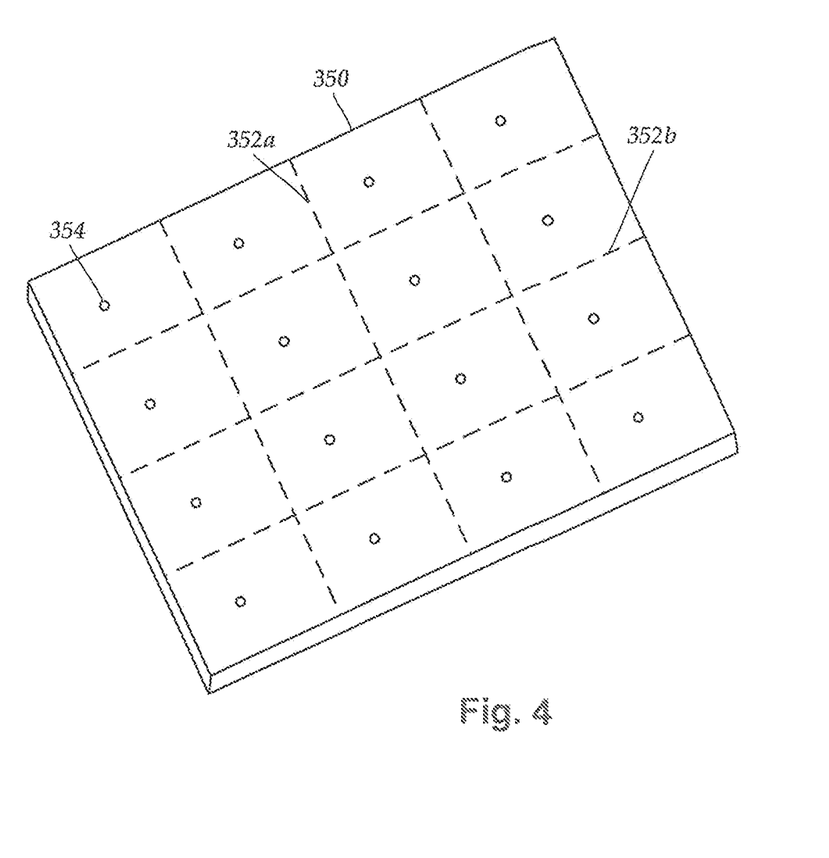
FIG. 4 is a schematic perspective view of another embodiment of a carrier for use in making a paddle of a paddle lead, according to the invention.

The perforations 352 can be arranged along one or more horizontal lines, as illustrated in FIG. 3A. FIG. 4 illustrates an alternative embodiment with perforations 352a, 352b along both horizontal and vertical lines. It will be understood that any other suitable arrangement of the perforations, including linear (e.g., only vertical lines or diagonal lines) or non-linear (e.g., concentric circles) arrangements, can be used. Moreover, the perforations may separate individual rows or columns of electrodes, but it will be understood that perforations can be formed between every second row or column, or every third row or column, or in any other regular or irregular pattern.

The holes 354 are optional and can pass entirely through the body of the carrier. In at least some embodiments, there is a hole for each electrode. In other embodiments, there may be fewer holes than electrodes. For example, there may be one hole for every two or three or four electrodes. As another example, there may be one or two holes for each column or row of electrodes.

Figure 3B:
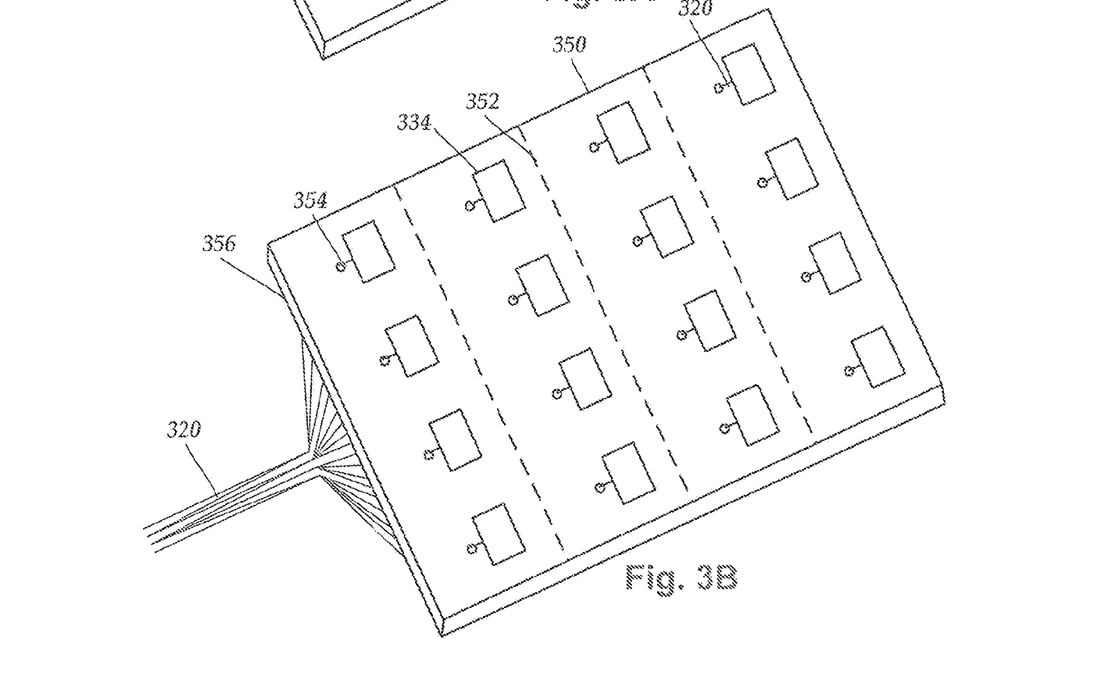
FIG. 3B is a schematic perspective view of the carrier of FIG. 3A with electrodes coupled to the carrier, according to the invention.

The electrodes 334 are attached, or otherwise coupled, to the carrier 350, as illustrated in FIG. 3B. In at least some embodiments, the electrodes 334 are attached to the carrier 350 by welding, soldering, adhesively binding, or mechanically coupling the electrodes to the carrier. In other embodiments, the electrodes 334 may be coupled to the carrier by pulling on the conductors 320 to hold the electrodes 334 in place. In yet other embodiments, the carrier 350 may include slots or other formations in the body of the carrier to receive the electrodes 334, or portions of the electrodes, and to hold the electrodes in place by friction or any other arrangement.

The electrodes 334 are also attached, or otherwise coupled, to conductors 320 that optionally pass through the holes 354 in the carrier and extend from one edge 356 of the carrier, as also illustrated in FIG. 3B. The conductors 320 can be single filar or multi-filar wires. The conductors 320 are typically coupled to the electrodes 334 using any suitable method including, but not limited to, welding, soldering, binding with a conductive adhesive, or the like.

In at least some embodiments, the conductors 320 pass through the holes 354 in the carrier 352. The conductors 320 may be coupled to the electrodes 334 prior to or after passing the conductors through the holes 354. In other embodiments, particularly those in which the carrier does not include the optional holes, the conductors 320 may pass over the surface of the carrier for attachment to the electrodes or may pass through the perforations for attachment to the electrodes.

Figures 3C, 3D:
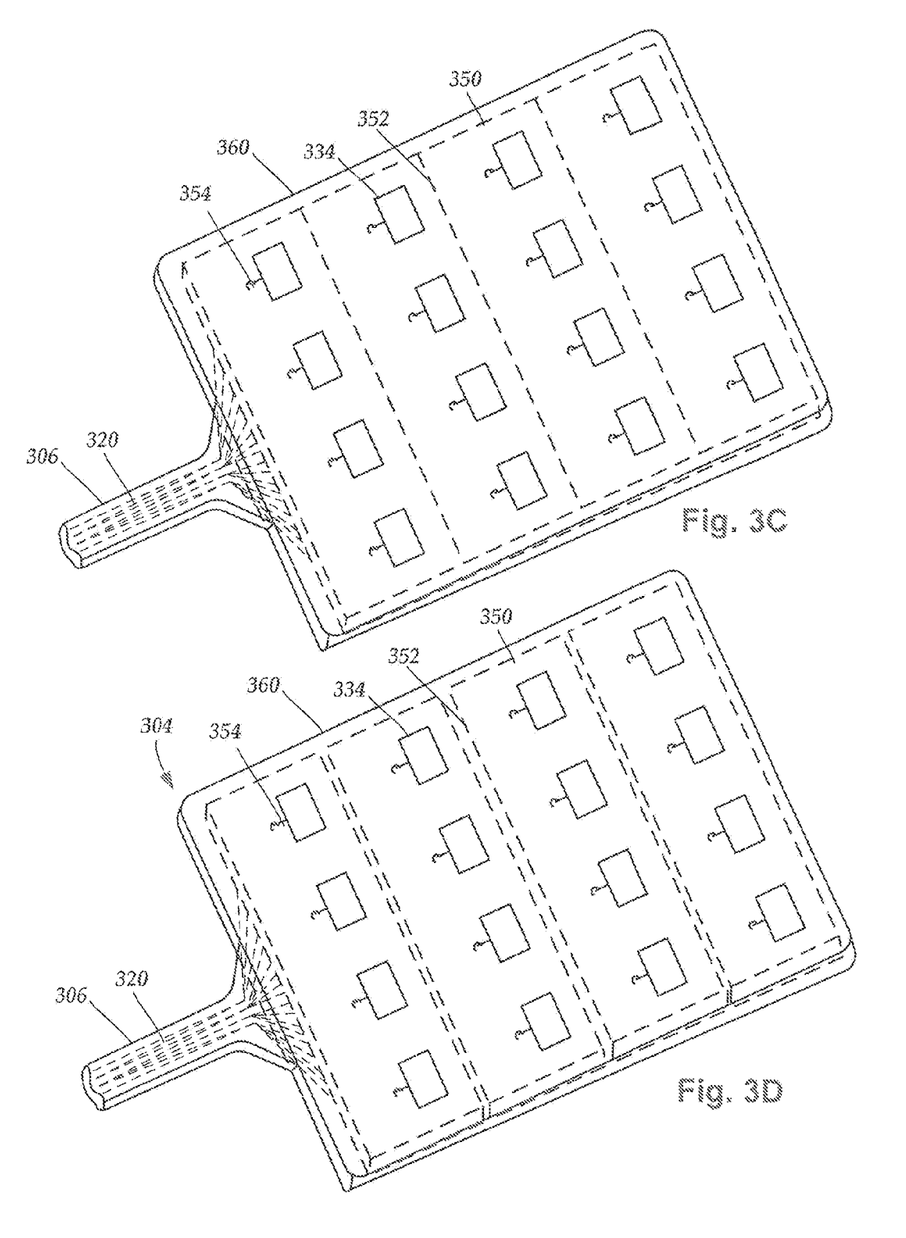
FIG. 3C is a schematic perspective view of the arrangement of FIG. 3B with a flexible paddle sheath formed around the carrier, according to the invention.
FIG. 3D is a schematic perspective view of the arrangement of FIG. 3C with the carrier broken along lines of perforations, according to the invention.

In at least some embodiments, the conductors 320 are directed to one edge 356 of the carrier 350 and gathered into one or more bundles that will be directed through one or more lead bodies 306 (see, FIG. 3C). It will be understood that other arrangements of the conductors can also be used.

After attaching or otherwise coupling the electrodes 334 to the conductors 320 and the carrier 350, a flexible paddle sheath 360 is formed over the carrier 350 and conductors 320 leaving a stimulation surface 358 of the electrodes 334 exposed, as illustrated FIG. 3C. The flexible paddle sheath 360 can be made of any suitable biocompatible, non-conductive material, such as, for example, silicon, polyurethane, or the like.

The flexible paddle sheath 360 may be formed by any suitable method including, but not limited to, molding (e.g., injection molding). The coupling the electrodes 334 to the carrier 350 facilitates maintenance of the relative positions of the electrodes 344 during formation of the flexible paddle sheath. In at least some embodiments, the carrier 350 and electrodes 334 are placed in a mold (for example, face down) so that the stimulation surfaces 358 of the electrodes is next to a surface of the mold to prevent or reduce the molding of material from the flexible paddle sheath onto the stimulation surfaces. In at least some embodiments, after formation of the flexible paddle sheath, excess material formed over the stimulation surfaces 358 of the electrodes 334 is removed. Such removal may include mechanical methods (e.g., grinding, scraping, or cutting with a tool) or chemical methods (e.g., etching or dissolving) of removal or cutting away the material using a laser or other device.

In at least some embodiments, one or more lead bodies 306, or portion(s) of the one or more lead bodies adjacent to the flexible paddle sheath 360, may be formed simultaneously with the flexible paddle sheath and around the one or more bundles of conductors 320 extending beyond the carrier, as illustrated in FIG. 3C.

After forming the flexible paddle sheath 360, the carrier 350 is broken along the perforations 352, as illustrated in FIG. 3D. The breakage of the carrier 350 can make the resulting paddle 304 more flexible. The flexibility may be in one or more directions, depending at least in part on the disposition of the perforations and how the carrier is broken.

Breakage of the carrier 350 can be accomplished using any suitable method including manual or mechanical breakage. For example, the paddle 304 may be bent over a rounded surface to break the carrier 350. In some embodiments, the paddle 304 may be bent one or more times in several different directions (for example, in each of two opposing directions) in order to induce breakage of the carrier 350.

It will be understood that the carrier 350 need not necessarily be broken entirely along each of the lines of perforations 352 or even entirely along any of the lines of perforations. The breakage along the lines of perforations may be partial. There will be, however, some degree of breakage to increase the flexibility of the resulting paddle 304. In some embodiments, however, the carrier is broken so that the carrier is separated into distinct portions along at least one (and preferably all) of the lines of perforations 352.

Figure 5:
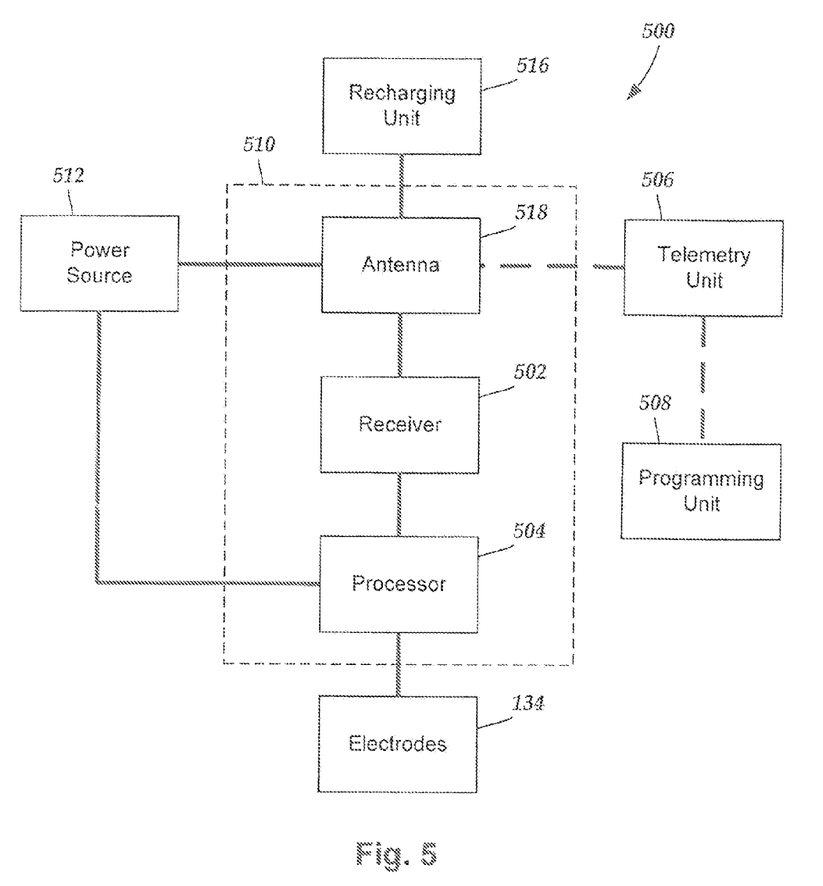
FIG. 5 is a schematic overview of one embodiment of components of a stimulation system, including an electronic subassembly disposed within a control module, according to the invention.

FIG. 5 is a schematic overview of one embodiment of components of an electrical stimulation system 500 including an electronic subassembly 510 disposed within a control module. It will be understood that the electrical stimulation system can include more, fewer, or different components and can have a variety of different configurations including those configurations disclosed in the stimulator references cited herein.

Some of the components (for example, a power source 512, an antenna 518, a receiver 502, and a processor 504) of the electrical stimulation system can be positioned on one or more circuit boards or similar carriers within a sealed housing of an implantable pulse generator, if desired. Any power source 512 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 518 or a secondary antenna. The external power source can be in a device that is mounted on the skin of the user or in a unit that is provided near the user on a permanent or periodic basis.

If the power source 512 is a rechargeable battery, the battery may be recharged using the optional antenna 518, if desired. Power can be provided to the battery for recharging by inductively coupling the battery through the antenna to a recharging unit 516 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 504 is generally included to control the timing and electrical characteristics of the electrical stimulation system. For example, the processor 504 can, if desired, control one or more of the timing, frequency, strength, duration, and waveform of the pulses. In addition, the processor 504 can select which electrodes can be used to provide stimulation, if desired. In some embodiments, the processor 504 selects which electrode(s) are cathodes and which electrode(s) are anodes. In some embodiments, the processor 504 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 508 that, for example, allows modification of pulse characteristics. In the illustrated embodiment, the processor 504 is coupled to a receiver 502 which, in turn, is coupled to the optional antenna 518. This allows the processor 504 to receive instructions from an external source to, for example, direct the pulse characteristics and the selection of electrodes, if desired.

In one embodiment, the antenna 518 is capable of receiving signals (e.g., RF signals) from an external telemetry unit 506 which is programmed by the programming unit 508. The programming unit 508 can be external to, or part of, the telemetry unit 506. The telemetry unit 506 can be a device that is worn on the skin of the user or can be carried by the user and can have a form similar to a pager, cellular phone, or remote control, if desired. As another alternative, the telemetry unit 506 may not be worn or carried by the user but may only be available at a home station or at a clinician's office. The programming unit 508 can be any unit that can provide information to the telemetry unit 506 for transmission to the electrical stimulation system 500. The programming unit 508 can be part of the telemetry unit 506 or can provide signals or information to the telemetry unit 506 via a wireless or wired connection. One example of a suitable programming unit is a computer operated by the user or clinician to send signals to the telemetry unit 506.

The signals sent to the processor 504 via the antenna 518 and the receiver 502 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 500 to cease operation, to start operation, to start charging the battery, or to stop charging the battery. In other embodiments, the stimulation system does not include the antenna 518 or receiver 502 and the processor 504 operates as programmed.

Optionally, the electrical stimulation system 500 may include a transmitter (not shown) coupled to the processor 504 and the antenna 518 for transmitting signals back to the telemetry unit 506 or another unit capable of receiving the signals. For example, the electrical stimulation system 500 may transmit signals indicating whether the electrical stimulation system 500 is operating properly or not or indicating when the battery needs to be charged or the level of charge remaining in the battery. The processor 504 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method of making an electrical stimulation lead, the method comprising:
   coupling a plurality of electrodes to a carrier, the carrier defining at least one set of perforations;
   coupling the plurality of electrodes to a plurality of conductors;
   forming a flexible paddle sheath surrounding the carrier leaving a stimulation surface of each of the plurality of electrodes exposed; and
   after forming the flexible paddle sheath, breaking the carrier along at least one of the at least one set of perforations leaving the flexible paddle sheath intact.

2. The method of claim 1, wherein the carrier defines a plurality of holes through the carrier, the method further comprising passing the plurality of conductors through the plurality of holes in the carrier.

3. The method of claim 1, wherein the at least one set of perforations comprises a plurality of sets of perforations, each set of perforations defining a line along the carrier.

4. The method of claim 3, wherein breaking the carrier comprises breaking the carrier along the lines defined by the plurality of sets of perforations.

5. A method of making an electrical stimulation lead, the method comprising:
   coupling a plurality of electrodes to a carrier, the carrier defining a plurality of sets of perforations, each set of perforations defining a line along the carrier;
   coupling the plurality of electrodes to a plurality of conductors;
   forming a flexible paddle sheath over the carrier leaving a stimulation surface of each of the plurality of electrodes exposed; and
   after forming the flexible paddle sheath, breaking the carrier along at least one of the at least one set of perforations, wherein the plurality of sets of perforations define at least one horizontal line along the carrier and at least one vertical line along the carrier.

6. The method of claim 1, wherein breaking the carrier comprises separating the carrier into at least two separated portions along at least one of the at least one set of perforations.

7. The method of claim 1, wherein coupling the plurality of electrodes to the carrier comprises attaching the plurality of electrodes to the carrier.

8. The method of claim 7, wherein attaching the plurality of electrodes to the carrier comprises welding the plurality of electrodes to the carrier.

9. The method of claim 1, wherein a material of the flexible paddle sheath is more flexible than a material of the carrier.

10. The method of claim 9, wherein the carrier is more rigid than the flexible paddle sheath.

11. The method of claim 1, wherein forming the flexible paddle sheath comprises forming the flexible paddle sheath by injection molding.

12. An electrical stimulation lead, comprising:
    a paddle body comprising a carrier and a flexible paddle sheath surrounding the carrier, wherein the carrier is broken into at least two pieces with the flexible paddle sheath remaining intact;
    at least one lead body having a distal end portion, a proximal end portion, and a longitudinal length, the distal ends of each of the at least one lead body coupled to the paddle body;
    a plurality of electrodes disposed on the paddle body and coupled to the carrier, wherein each electrode has a stimulation surface that is exposed through the flexible paddle sheath;
    a plurality of terminals disposed along the proximal end portions of each of the at least one lead body; and
    a plurality of conductors electrically coupling the plurality of terminals to the plurality of electrodes.

13. The electrical stimulation lead of claim 12, wherein the flexible paddle sheath is more flexible than the carrier.

14. The electrical stimulation lead of claim 13, wherein the carrier is more rigid than the flexible paddle sheath.

15. The electrical stimulation lead of claim 12, wherein the electrodes are attached to the carrier.

16. The electrical stimulation lead of claim 15, wherein the electrodes are welded to the carrier.

17. The electrical stimulation lead of claim 15, wherein the at least two pieces of the carrier comprise a first piece and a second piece and wherein at least one of the plurality of electrodes is attached to the first piece and at least one of the plurality of electrodes is attached to the second piece.

18. The electrical stimulation lead of claim 12, wherein the at least two pieces of the carrier comprise a plurality of pieces that are horizontally separated from each other.

19. An electrical stimulating system comprising:
    the electrical stimulation lead of claim 12;
    a control module coupleable to the electrical stimulation lead, the control module comprising
        a housing, and
        an electronic subassembly disposed in the housing; and
    a connector for receiving the electrical stimulation lead, the connector having a proximal end, a distal end, and a longitudinal length, the connector comprising
        a connector housing defining a port at the distal end of the connector, the port configured and arranged for receiving the proximal end of the lead body of the electrical stimulation lead, and
        a plurality of connector contacts disposed in the connector housing, the plurality of connector contacts configured and arranged to couple to at least one of the plurality of terminals disposed on the proximal end of the lead body of the electrical stimulation lead.

20. The electrical stimulation system of claim 19, further comprising a lead extension coupleable to both the electrical stimulation lead and the control module.

* * * * *